(12) United States Patent
Rezajoo

(10) Patent No.: US 12,718,290 B2
(45) Date of Patent: Aug. 25, 2026

(54) MACHINE LEARNING MODEL

(71) Applicant: Truist Bank, Charlotte, NC (US)

(72) Inventor: Ali Rezajoo, Charlotte, NC (US)

(73) Assignee: TRUIST BANK, Charlotte, NC (US)

( * ) Notice: Subject to any disclaimer, the term of this patent is extended or adjusted under 35 U.S.C. 154(b) by 0 days.

(21) Appl. No.: 18/624,365

(22) Filed: Apr. 2, 2024

(65) Prior Publication Data

US 2025/0307914 A1 Oct. 2, 2025

(51) Int. Cl.
*G06Q 40/02* (2023.01)
*A61B 5/00* (2006.01)
*G06Q 40/03* (2023.01)

(52) U.S. Cl.
CPC ............. *G06Q 40/02* (2013.01); *A61B 5/681* (2013.01); *G06Q 40/03* (2023.01)

(58) Field of Classification Search
None
See application file for complete search history.

(56) References Cited

U.S. PATENT DOCUMENTS 11,727,483 B1 * 8/2023 Eidam .................. G06Q 30/016 705/44
2017/0169379 A1 * 6/2017 Horseman .............. G06Q 10/00
2020/0104935 A1 * 4/2020 Schmitt .................. G06Q 40/02
2022/0076834 A1 * 3/2022 Hanlon, Jr. ............ G16H 50/20
2023/0054609 A1 * 2/2023 Tayeb ................... G06F 18/214
2024/0242272 A1 * 7/2024 Toscano ................. G06Q 40/03

OTHER PUBLICATIONS

M. Radlinger, Facts About Fitness Trackers and Which One is Right for You, capture of URL from Dec. 4, 2023 originally published May 15, 2020 retrieved from https://web.archive.org/web/20231204190200/https://networkhealth.com/grow-in-the-know/2020/05/facts-about-fitness-trackers-and-which-one-is-right- (Year: 2023).*

* cited by examiner

*Primary Examiner* — Gregory S Cunningham, II
(74) *Attorney, Agent, or Firm* — Michael A. Springs, Esq.; Shumaker, Loop & Kendrick, LLP; Patrick B. Horne

(57) ABSTRACT

A system and method that evaluate and monitor the financial and physical wellbeing of a person that is a client of a bank, and provides a financial wellness score that is used to provide banking service recommendations that may act to increase the wellness score. The method includes collecting data and information about a financial wellbeing of the person, assigning a financial wellbeing score to the person based on the collected data and information about the financial wellbeing of the person, collecting data and information about a physical wellbeing of the person, assigning a physical wellbeing score to the person based on the collected data and information about the physical wellbeing of the person, and combining the financial wellbeing score and the physical wellbeing score to obtain a financial wellness score that provides an indication of the financial wellness of the person.

20 Claims, 7 Drawing Sheets

MACHINE LEARNING MODEL

BACKGROUND

Field

This disclosure relates generally to a combined financial and wellness scoring system that evaluates and monitors the financial and physical wellbeing of a person and, more particularly, to a combined financial and wellness scoring system that evaluates and monitors the financial and physical wellbeing of a person that is a client of a bank, and provides a financial wellness score that is used to provide banking service recommendations that may act to increase the wellness score.

Discussion

A bank is a financial institution that is licensed to receive deposits from individuals and organizations and to make loans to those individuals and organizations or others. Banks may also perform other services such as wealth management, currency exchange, etc. Therefore, a bank may have thousands of customers and clients. Depending on the services that a bank provides, it may be classified as a retail bank, a commercial bank, an investment bank or some combination thereof. A retail bank typically provides services such as checking and savings accounts, loan and mortgage services, financing for automobiles, and short-term loans such as overdraft protection. A commercial bank typically provides credit services, cash management, commercial real estate services, employer services, trade finance, etc. An investment bank typically provides corporate clients with complex services and financial transactions such as underwriting and assisting with merger and acquisition activity.

Banks provide a number of financial products and services to their clients. As a person travels through life various major life events periodically occur, such as enrolling in college, buying a car, getting married, buying a home, having children, starting a business, retiring, etc. Because of these events, the financial products and services that a person needs generally changes, such as the need to obtain a mortgage, the need to obtain a student loan, etc. Banks often use a conversation guide, sometimes referred to as a digital client conversation guide (DCCG), that directs bank employees to ask questions of the bank's clients to identify such life events so that the bank understands the client's needs and directs them to the right products and services for those needs. For example, banks have been known to use the Myday™ app to provide such questions, recommendations and solutions for their clients, where the Myday™ app provides an easy-to-use, personalized and effective system to manage what a person needs for a particular thing in one place.

A significant portion of Americans experience financial stress either continuously or intermittently. This financial stress can come from a variety of factors, such as living paycheck to paycheck, credit card debt, student loan debt, retirement anxiety, insufficient savings, worrying about losing a job, etc. For example, studies have shown that 74% of Americans live paycheck to paycheck, 40% of Americans would have difficulty covering an unexpected $400 expense without selling something or borrowing money, 68% of Americans feel anxiety about having enough saved for retirement and half of Americans have no retirement savings at all. Further, many Americans, especially younger Americans, often lack adequate knowledge about financial matters.

SUMMARY

The following discussion discloses and describes a combined financial and wellness scoring system and related method that evaluate and monitor the financial and physical wellbeing of a person that is a client of a bank, and provides a financial wellness score that is used to provide banking service recommendations that may act to increase the wellness score. The method includes collecting data and information about a financial wellbeing of the person from a client central database that stores name, address, birthdate, account types, account balances, social security number and credit scores for clients of the bank, from a client interaction and transaction source that stores information and data obtained for each of the interactions and transactions between all of the banks clients and the bank over all of the banking channels, and from a financial monitoring source that provides significant credit score changes, changes in direct deposit patterns or income changes including loss of employment and reduction in work hours, changes in transaction and account patterns including account closures, frequent overdrafts, late payments and sudden increase in debt-related transactions, changes in credit card patterns including increased transaction frequency for basic needs with decreased spending in dining out and entertainment, sale of investments or assets, requests for payment extensions or loan modifications, and payday loads or cash advances, and assigning a financial wellbeing score to the person based on the collected data and information about the financial wellbeing of the person. The method further includes collecting data and information about a physical wellbeing of the person from a wearable device that collects one or more of increased/reduced heart rate, changes in skin condition, such as from sweating and temperature changes, alterations in sleep patterns including difficulty in sleeping and restlessness, blood pressure, diet-related factors and muscle tension and pain, and assigning a physical wellbeing score to the person based on the collected data and information about the physical wellbeing of the person. The method combines the financial wellbeing score and the physical wellbeing score to obtain a financial wellness score that provides an indication of the financial wellness of the person.

Additional features of the disclosure will become apparent from the following description and appended claims, taken in conjunction with the accompanying drawings.

DETAILED DESCRIPTION OF THE EMBODIMENTS

Figure 1:
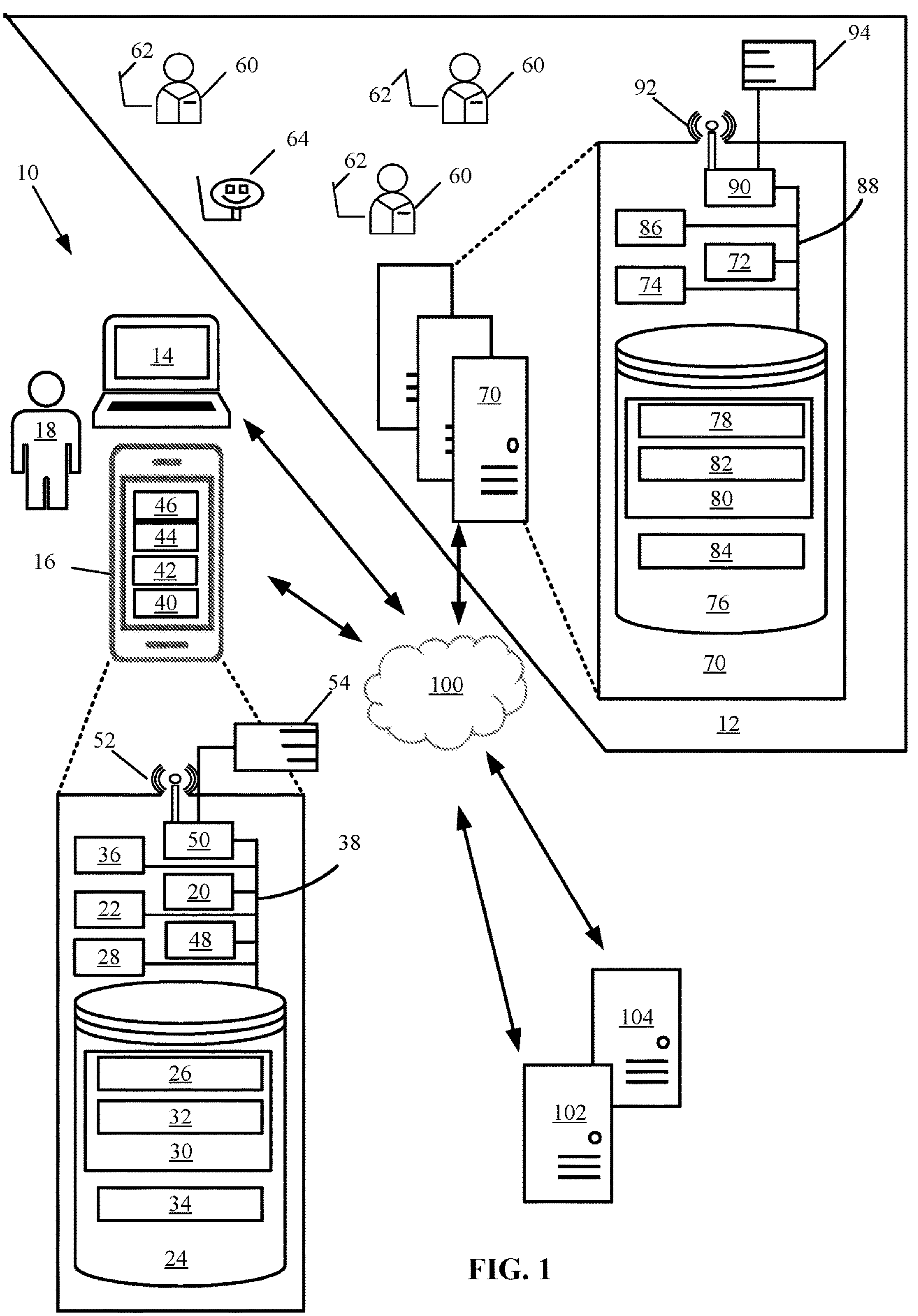
FIG. 1 illustrates a system and environment thereof by which a user benefits through use of services and products of an enterprise system.

The following discussion of the embodiments of the disclosure directed to a combined financial and wellness scoring system that evaluates and monitors the financial and physical wellbeing of a person that is a client of a bank, and provides a wellness score that is used to provide banking service recommendations that may increase the wellness score is merely exemplary in nature, and is in no way intended to limit the disclosure or its applications or uses.

Embodiments of the present disclosure will now be described more fully hereinafter with reference to the accompanying drawings, in which some, but not all, embodiments of the disclosure are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout. Unless described or implied as exclusive alternatives, features throughout the drawings and descriptions should be taken as cumulative, such that features expressly associated with some particular embodiments can be combined with other embodiments. Unless defined otherwise, technical and scientific terms used herein have the same meaning as commonly understood to one of ordinary skill in the art to which the presently disclosed subject matter pertains.

The exemplary embodiments are provided so that this disclosure will be both thorough and complete, and will fully convey the scope of the disclosure and enable one of ordinary skill in the art to make, use and practice the disclosure.

The terms "coupled," "fixed," "attached to," "communicatively coupled to," "operatively coupled to," and the like refer to both (i) direct connecting, coupling, fixing, attaching, communicatively coupling; and (ii) indirect connecting coupling, fixing, attaching, communicatively coupling via one or more intermediate components or features, unless otherwise specified herein. "Communicatively coupled to" and "operatively coupled to" can refer to physically and/or electrically related components.

Embodiments of the present disclosure described herein, with reference to flowchart illustrations and/or block diagrams of methods or apparatuses (the term "apparatus" includes systems and computer program products), will be understood such that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a particular machine, such that the instructions, which execute via the processor of the computer or other programmable data processing apparatus, create mechanisms for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer readable memory produce an article of manufacture including instructions, which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions, which execute on the computer or other programmable apparatus, provide steps for implementing the functions/acts specified in the flowchart and/or block diagram block or blocks. Alternatively, computer program implemented steps or acts may be combined with operator or human implemented steps or acts in order to carry out an embodiment of the disclosure.

While certain exemplary embodiments have been described and shown in the accompanying drawings, it is to be understood that such embodiments are merely illustrative of, and not restrictive on, the broad disclosure, and that this disclosure not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the herein described embodiments can be configured without departing from the scope and spirit of the disclosure. Therefore, it is to be understood that, within the scope of the included claims, the disclosure may be practiced other than as specifically described herein.

FIG. 1 illustrates a system 10, such as a banking system, and environment thereof by which a user 18 benefits through use of services and products of an enterprise system 12. The user 18 accesses services and products by use of one or more user devices, illustrated in separate examples as a computing device 14 and a mobile device 16, which may be, as non-limiting examples, a smart phone, a portable digital assistant (PDA), a pager, a mobile television, a gaming device, a laptop computer, a camera, a video recorder, an audio/video player, radio, a GPS device, or any combination of the aforementioned, or other portable device with processing and communication capabilities. In the illustrated example, the mobile device 16 is the system 10 as having exemplary elements, the below descriptions of which apply as well to the computing device 14, which can be, as non-limiting examples, a desktop computer, a laptop computer or other user-accessible computing device.

Furthermore, the user device, referring to either or both of the computing device 14 and the mobile device 16, may be or include a workstation, a server, or any other suitable device, including a set of servers, a cloud-based application or system, or any other suitable system, adapted to execute, for example any suitable operating system, including Linux, UNIX, Windows, macOS, IOS, Android and any other known operating system used on personal computers, central computing systems, phones, and other devices.

The user 18 can be an individual, a group or any entity in possession of or having access to the user device, referring to either or both of the computing device 14 and the mobile device 16, which may be personal or public items. Although the user 18 may be singly represented in some drawings, at least in some embodiments according to these descriptions the user 18 is one of many such that a market or community of users, consumers, customers, business entities, government entities, clubs, and groups of any size are all within the scope of these descriptions.

The user device, as illustrated with reference to the mobile device 16, includes components such as at least one of each of a processing device 20, and a memory device 22 for processing use, such as random access memory (RAM), and read-only memory (ROM). The illustrated mobile device 16 further includes a storage device 24 including at least one of a non-transitory storage medium, such as a microdrive, for long-term, intermediate-term, and short-term storage of computer-readable instructions 26 for execution by the processing device 20. For example, the instructions 26 can include instructions for an operating system and various applications or programs 30, of which the application 32 is represented as a particular example. The storage device 24 can store various other data items 34, which can include, as non-limiting examples, cached data, user files such as those for pictures, audio and/or video recordings, files downloaded or received from other devices, and other data items preferred by the user or required or related to any or all of the applications or programs 30.

The memory device 22 is operatively coupled to the processing device 20. As used herein, memory includes any computer readable medium to store data, code, or other information. The memory device 22 may include volatile memory, such as volatile RAM including a cache area for the temporary storage of data. The memory device 22 may also include non-volatile memory, which can be embedded and/or may be removable. The non-volatile memory can additionally or alternatively include an electrically erasable programmable read-only memory (EEPROM), flash memory or the like.

The memory device 22 and the storage device 24 can store any of a number of applications that comprise computer-executable instructions and code executed by the processing device 20 to implement the functions of the mobile device 16 described herein. For example, the memory device 22 may include such applications as a conventional web browser application and/or a mobile P2P payment system client application. These applications also typically provide a graphical user interface (GUI) on a display 40 that allows the user 18 to communicate with the mobile device 16, and, for example, a mobile banking system, and/or other devices or systems. In one embodiment, when the user 18 decides to enroll in a mobile banking program, the user 18 downloads or otherwise obtains the mobile banking system client application from a mobile banking system, for example, the enterprise system 12, or from a distinct application server. In other embodiments, the user 18 interacts with a mobile banking system via a web browser application in addition to, or instead of, the mobile P2P payment system client application.

The processing device 20, and other processors described herein, generally include circuitry for implementing communication and/or logic functions of the mobile device 16. For example, the processing device 20 may include a digital signal processor, a microprocessor, and various analog to digital converters, digital to analog converters, and/or other support circuits. Control and signal processing functions of the mobile device 16 are allocated between these devices according to their respective capabilities. The processing device 20 thus may also include the functionality to encode and interleave messages and data prior to modulation and transmission. The processing device 20 can additionally include an internal data modem. Further, the processing device 20 may include functionality to operate one or more software programs, which may be stored in the memory device 22, or in the storage device 24. For example, the processing device 20 may be capable of operating a connectivity program, such as a web browser application. The web browser application may then allow the mobile device 16 to transmit and receive web content, such as, for example, location-based content and/or other web page content, according to a wireless application protocol (WAP), hypertext transfer protocol (HTTP), and/or the like.

The memory device 22 and the storage device 24 can each also store any of a number of pieces of information, and data, used by the user device and the applications and devices that facilitate functions of the user device, or are in communication with the user device, to implement the functions described herein and others not expressly described. For example, the storage device 24 may include such data as user authentication information, etc.

The processing device 20, in various examples, can operatively perform calculations, can process instructions for execution and can manipulate information. The processing device 20 can execute machine-executable instructions stored in the storage device 24 and/or the memory device 22 to thereby perform methods and functions as described or implied herein, for example, by one or more corresponding flow charts expressly provided or implied as would be understood by one of ordinary skill in the art to which the subject matters of these descriptions pertain. The processing device 20 can be or can include, as non-limiting examples, a central processing unit (CPU), a microprocessor, a graphics processing unit (GPU), a microcontroller, an application-specific integrated circuit (ASIC), a programmable logic device (PLD), a digital signal processor (DSP), a field programmable gate array (FPGA), a state machine, a controller, gated or transistor logic, discrete physical hardware components, and combinations thereof. In some embodiments, particular portions or steps of methods and functions described herein are performed in whole or in part by way of the processing device 20, while in other embodiments methods and functions described herein include cloud-based computing in whole or in part such that the processing device 20 facilitates local operations including, as non-limiting examples, communication, data transfer, and user inputs and outputs such as receiving commands from and providing displays to the user.

The mobile device 16, as illustrated, includes an input and output system 36, referring to, including, or operatively coupled with, user input devices and user output devices, which are operatively coupled to the processing device 20. The user output devices include the display 40 (e.g., a liquid crystal display or the like), which can be, as a non-limiting example, a touch screen of the mobile device 16, which serves both as an output device, by providing graphical and text indicia and presentations for viewing by one or more of the users 18, and as an input device, by providing virtual buttons, selectable options, a virtual keyboard, and other indicia that, when touched, control the mobile device 16 by user action. The user output devices include a speaker 44 or other audio device. The user input devices, which allow the mobile device 16 to receive data and actions such as button manipulations and touches from a user such as the user 18, may include any of a number of devices allowing the mobile device 16 to receive data from a user, such as a keypad, keyboard, touch-screen, touchpad, microphone 42, mouse, joystick, other pointer device, button, soft key, and/or other input device(s). The user interface may also include a camera 46, such as a digital camera.

Further non-limiting examples include one or more of each, any and all of a wireless or wired keyboard, a mouse, a touchpad, a button, a switch, a light, an LED, a buzzer, a bell, a printer and/or other user input devices and output devices for use by or communication with the user 18 in accessing, using, and controlling, in whole or in part, the user device, referring to either or both of the computing device 14 and the mobile device 16. Inputs by one or more of the users 18 can thus be made via voice, text or graphical indicia selections. For example, such inputs in some examples correspond to user-side actions and communications seeking services and products of the enterprise system 12, and at least some outputs in such examples correspond to data representing enterprise-side actions and communications in two-way communications between the user 18 and the enterprise system 12.

The mobile device 16 may also include a positioning system device 48, which can be, for example, a global positioning system (GPS) device configured to be used by a positioning system to determine a location of the mobile device 16. For example, the positioning system device 48 may include a GPS transceiver. In some embodiments, the positioning system device 48 includes an antenna, transmitter, and receiver. For example, in one embodiment, triangulation of cellular signals may be used to identify the approximate location of the mobile device 16. In other embodiments, the positioning device 48 includes a proximity sensor or transmitter, such as an RFID tag, that can sense or be sensed by devices known to be located proximate a merchant or other location to determine that the consumer mobile device 16 is located proximate these known devices.

In the illustrated example, a system intraconnect 38 connects, for example electrically, the various described, illustrated, and implied components of the mobile device 16. The intraconnect 38, in various non-limiting examples, can include or represent, a system bus, a high-speed interface connecting the processing device 20 to the memory device 22, individual electrical connections among the components, and electrical conductive traces on a motherboard common to some or all of the above-described components of the user device. As discussed herein, the system intraconnect 38 may operatively couple various components with one another, or in other words, electrically connects those components, either directly or indirectly—by way of intermediate component(s)—with one another.

The user device, referring to either or both of the computing device 14 and the mobile device 16, with particular reference to the mobile device 16 for illustration purposes, includes a communication interface 50, by which the mobile device 16 communicates and conducts transactions with other devices and systems. The communication interface 50 may include digital signal processing circuitry and may provide two-way communications and data exchanges, for example, wirelessly via wireless communication device 52, and for an additional or alternative example, via wired or docked communication by mechanical electrically conductive connector 54. Communications may be conducted via various modes or protocols, of which GSM voice calls, SMS, EMS, MMS messaging, TDMA, CDMA, PDC, WCDMA, CDMA2000, and GPRS, are all non-limiting and non-exclusive examples. Thus, communications can be conducted, for example, via the wireless communication device 52, which can be or include a radio-frequency transceiver, a Bluetooth device, Wi-Fi device, a near-field communication device, and other transceivers. In addition, GPS may be included for navigation and location-related data exchanges, ingoing and/or outgoing. Communications may also or alternatively be conducted via the connector 54 for wired connections such by USB, Ethernet, and other physically connected modes of data transfer.

The processing device 20 is configured to use the communication interface 50 as, for example, a network interface to communicate with one or more other devices on a network. In this regard, the communication interface 50 utilizes the wireless communication device 52 as an antenna operatively coupled to a transmitter and a receiver (together a "transceiver") included with the communication interface 50. The processing device 20 is configured to provide signals to and receive signals from the transmitter and receiver, respectively. The signals may include signaling information in accordance with the air interface standard of the applicable cellular system of a wireless telephone network. In this regard, the mobile device 16 may be configured to operate with one or more air interface standards, communication protocols, modulation types, and access types. By way of illustration, the mobile device 16 may be configured to operate in accordance with any of a number of first, second, third, fourth or fifth-generation communication protocols and/or the like. For example, the mobile device 16 may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as universal mobile telecommunications System (UMTS), CDMA2000, wideband CDMA (WCDMA) and/or time division-synchronous CDMA (TD-SCDMA), with fourth-generation (4G) wireless communication protocols such as long-term evolution (LTE), fifth-generation (5G) wireless communication protocols, Bluetooth low energy (BLE) communication protocols such as Bluetooth 5.0, ultra-wideband (UWB) communication protocols, and/or the like. The mobile device 16 may also be configured to operate in accordance with non-cellular communication mechanisms, such as via a wireless local area network (WLAN) or other communication/data networks.

The communication interface 50 may also include a payment network interface. The payment network interface may include software, such as encryption software, and hardware, such as a modem, for communicating information to and/or from one or more devices on a network. For example, the mobile device 16 may be configured so that it can be used as a credit or debit card by, for example, wirelessly communicating account numbers or other authentication information to a terminal of the network. Such communication could be performed via transmission over a wireless communication protocol such as the Near-field communication protocol.

The mobile device 16 further includes a power source 28, such as a battery, for powering various circuits and other devices that are used to operate the mobile device 16. Embodiments of the mobile device 16 may also include a clock or other timer configured to determine and, in some cases, communicate actual or relative time to the processing device 20 or one or more other devices. For a further example, the clock may facilitate timestamping transmissions, receptions, and other data for security, authentication, logging, polling, data expiry and forensic purposes.

The system 10 as illustrated diagrammatically represents at least one example of a possible implementation, where alternatives, additions, and modifications are possible for performing some or all of the described methods, operations and functions. Although shown separately, in some embodiments, two or more systems, servers, or illustrated components may utilized. In some implementations, the functions of one or more systems, servers, or illustrated components may be provided by a single system or server. In some embodiments, the functions of one illustrated system or server may be provided by multiple systems, servers, or computing devices, including those physically located at a central facility, those logically local, and those located as remote with respect to each other.

The enterprise system 12 can offer any number or type of services and products to one or more of the users 18. In some examples, the enterprise system 12 offers products, and in some examples, the enterprise system 12 offers services. Use of "service(s)" or "product(s)" thus relates to either or both in these descriptions. With regard, for example, to online information and financial services, "service" and "product" are sometimes termed interchangeably. In non-limiting examples, services and products include retail services and products, information services and products, custom services and products, predefined or pre-offered services and products, consulting services and products, advising services and products, forecasting services and products, internet products and services, social media, and financial services and products, which may include, in non-limiting examples, services and products relating to banking, checking, savings, investments, credit cards, automatic-teller machines, debit cards, loans, mortgages, personal accounts, business accounts, account management, credit reporting, credit requests and credit scores.

To provide access to, or information regarding, some or all the services and products of the enterprise system 12, automated assistance may be provided by the enterprise system 12. For example, automated access to user accounts and replies to inquiries may be provided by enterprise-side automated voice, text, and graphical display communications and interactions. In at least some examples, any number of human agents 60 can be employed, utilized, authorized or referred by the enterprise system 12. Such human agents 60 can be, as non-limiting examples, point of sale or point of service (POS) representatives, online customer service assistants available to the users 18, advisors, managers, sales team members, and referral agents ready to route user requests and communications to preferred or particular other agents, human or virtual.

The human agents 60 may utilize agent devices 62 to serve users in their interactions to communicate and take action. The agent devices 62 can be, as non-limiting examples, computing devices, kiosks, terminals, smart devices such as phones, and devices and tools at customer service counters and windows at POS locations. In at least one example, the diagrammatic representation of the components of the mobile device 16 in FIG. 1 applies as well to one or both of the computing device 14 and the agent devices 62.

The agent devices 62 individually or collectively include input devices and output devices, including, as non-limiting examples, a touch screen, which serves both as an output device by providing graphical and text indicia and presentations for viewing by one or more of the agents 60, and as an input device by providing virtual buttons, selectable options, a virtual keyboard, and other indicia that, when touched or activated, control or prompt the agent device 62 by action of the attendant agent 60. Further non-limiting examples include, one or more of each, any, and all of a keyboard, a mouse, a touchpad, a joystick, a button, a switch, a light, an LED, a microphone serving as input device for example for voice input by the human agent 60, a speaker serving as an output device, a camera serving as an input device, a buzzer, a bell, a printer and/or other user input devices and output devices for use by or communication with the human agent 60 in accessing, using, and controlling, in whole or in part, the agent device 62.

Inputs by one or more of the human agents 60 can thus be made via voice, text or graphical indicia selections. For example, some inputs received by the agent device 62 in some examples correspond to, control, or prompt enterprise-side actions and communications offering services and products of the enterprise system 12, information thereof, or access thereto. At least some outputs by the agent device 62 in some examples correspond to, or are prompted by, user-side actions and communications in two-way communications between the user 18 and an enterprise-side human agent 60.

From a user perspective experience, an interaction in some examples within the scope of these descriptions begins with direct or first access to one or more of the human agents 60 in person, by phone or online for example via a chat session or website function or feature. In other examples, a user is first assisted by a virtual agent 64 of the enterprise system 12, which may satisfy user requests or prompts by voice, text or online functions, and may refer users to one or more of the human agents 60 once preliminary determinations or conditions are made or met.

The enterprise system 12 includes a computing system 70 having various components, such as a processing device 72 and a memory device 74 for processing use, such as random access memory (RAM) and read-only memory (ROM). The computing system 70 further includes a storage device 76 having at least one non-transitory storage medium, such as a microdrive, for long-term, intermediate-term, and short-term storage of computer-readable instructions 78 for execution by the processing device 72. For example, the instructions 78 can include instructions for an operating system and various applications or programs 80, of which an application 82 is represented as a particular example. The storage device 76 can store various other data 84, which can include, as non-limiting examples, cached data, and files such as those for user accounts, user profiles, account balances, and transaction histories, files downloaded or received from other devices, and other data items preferred by the user or required or related to any or all of the applications or programs 80.

The computing system 70, in the illustrated example, also includes an input/output system 86, referring to, including, or operatively coupled with input devices and output devices such as, in a non-limiting example, agent devices 62, which have both input and output capabilities.

In the illustrated example, a system intraconnect 88 electrically connects the various above-described components of the computing system 70. In some cases, the intraconnect 88 operatively couples components to one another, which indicates that the components may be directly or indirectly connected, such as by way of one or more intermediate components. The intraconnect 88, in various non-limiting examples, can include or represent, a system bus, a high-speed interface connecting the processing device 72 to the memory device 74, individual electrical connections among the components, and electrical conductive traces on a motherboard common to some or all of the above-described components of the user device.

The computing system 70 includes a communication interface 90 by which the computing system 70 communicates and conducts transactions with other devices and systems. The communication interface 90 may include digital signal processing circuitry and may provide two-way communications and data exchanges, for example wirelessly via wireless device 92, and for an additional or alternative example, via wired or docked communication by mechanical electrically conductive connector 94. Communications may be conducted via various modes or protocols, of which GSM voice calls, SMS, EMS, MMS messaging, TDMA, CDMA, PDC, WCDMA, CDMA2000, and GPRS, are all non-limiting and non-exclusive examples. Thus, communications can be conducted, for example, via the wireless device 92, which can be or include a radio-frequency transceiver, a Bluetooth device, Wi-Fi device, near-field communication device, and other transceivers. In addition, GPS may be included for navigation and location-related data exchanges, ingoing and/or outgoing. Communications may also or alternatively be conducted via the connector 94 for wired connections such as by USB, Ethernet, and other physically connected modes of data transfer.

The processing device 72, in various examples, can operatively perform calculations, can process instructions for execution, and can manipulate information. The processing device 72 can execute machine-executable instructions stored in the storage device 76 and/or the memory device 74 to thereby perform methods and functions as described or implied herein, for example by one or more corresponding flow charts expressly provided or implied as would be understood by one of ordinary skill in the art to which the subjects matters of these descriptions pertain. The processing device 72 can be or can include, as non-limiting examples, a central processing unit (CPU), a microprocessor, a graphics processing unit (GPU), a microcontroller, an application-specific integrated circuit (ASIC), a programmable logic device (PLD), a digital signal processor (DSP), a field programmable gate array (FPGA), a state machine, a controller, gated or transistor logic, discrete physical hardware components, and combinations thereof.

Furthermore, the computing system 70, may be or include a workstation, a server, or any other suitable device, including a set of servers, a cloud-based application or system, or any other suitable system, adapted to execute, for example any suitable operating system, including Linux, UNIX, Windows, macOS, iOS, Android, and any known other operating system used on personal computer, central computing systems, phones, and other devices.

The user devices, referring to either or both of the mobile device 16 and the computing device 14, the agent devices 62 and the computing system 70, which may be one or any number centrally located or distributed, are in communication through one or more networks, referenced as system 10 in FIG. 1.

The network 100 provides wireless or wired communications among the components of the network 100 and the environment thereof, including other devices local or remote to those illustrated, such as additional mobile devices, servers, and other devices communicatively coupled to the network 100, including those not illustrated in FIG. 1. The network 100 is singly depicted for illustrative convenience, but may include more than one network without departing from the scope of these descriptions. In some embodiments, the network 100 may be or provide one or more cloud-based services or operations. The network 100 may be or include an enterprise or secured network, or may be implemented, at least in part, through one or more connections to the Internet. A portion of the network 100 may be a virtual private network (VPN) or an Intranet. The network 100 can include wired and wireless links, including, as non-limiting examples, 802.11a/b/g/n/ac, 802.20, WiMax, LTE, and/or any other wireless link. The network 100 may include any internal or external network, networks, sub-network, and combinations of such operable to implement communications between various computing components within and beyond the network 100. The network 100 may communicate, for example, internet protocol (IP) packets, frame relay frames, asynchronous transfer mode (ATM) cells, voice, video, data, and other suitable information between network addresses. The network 100 may also include one or more local area networks (LANs), radio access networks (RANs), metropolitan area networks (MANs), wide area networks (WANs), all or a portion of the internet and/or any other communication system or systems at one or more locations.

Two external systems 102 and 104 are illustrated in FIG. 1 and representing any number and variety of data sources, users, consumers, customers, business entities, banking systems, government entities, clubs, and groups of any size are all within the scope of the descriptions. In at least one example, the external systems 102 and 104 represent automatic teller machines (ATMs) utilized by the enterprise system 12 in serving the users 18. In another example, the external systems 102 and 104 represent payment clearinghouse or payment rail systems for processing payment transactions, and in another example, the external systems 102 and 104 represent third party systems such as merchant systems configured to interact with the user device 16 during transactions and also configured to interact with the enterprise system 12 in back-end transactions clearing processes.

In certain embodiments, one or more of the systems such as the user device 16, the enterprise system 12, and/or the external systems 102 and 104 are, include, or utilize virtual resources. In some cases, such virtual resources are considered cloud resources or virtual machines. Such virtual resources may be available for shared use among multiple distinct resource consumers and in certain implementations, virtual resources do not necessarily correspond to one or more specific pieces of hardware, but rather to a collection of pieces of hardware operatively coupled within a cloud computing configuration so that the resources may be shared as needed.

As used herein, an artificial intelligence (AI) system, artificial intelligence algorithm, artificial intelligence module, artificial intelligence program, and the like, generally refer to computer implemented programs that are suitable to simulate intelligent behavior (i.e., intelligent human behavior) and/or computer systems and associated programs suitable to perform tasks that typically require a human to perform, such as tasks requiring visual perception, speech recognition, decision-making, translation, and the like. An artificial intelligence system may include, for example, at least one of a series of associated if-then logic statements, a statistical model suitable to map raw sensory data into symbolic categories and the like, or a machine learning program. A machine learning program, machine learning algorithm, or machine learning module, as used herein, is generally a type of artificial intelligence including one or more algorithms that can learn and/or adjust parameters based on input data provided to the algorithm. In some instances, machine learning programs, algorithms and modules are used at least in part in implementing artificial intelligence (AI) functions, systems and methods.

Artificial Intelligence and/or machine learning models and programs may be associated with or conducted by one or more processors, memory devices, and/or storage devices of a computing system or device. It should be appreciated that the artificial intelligence algorithm or program may be incorporated within the existing system architecture or be configured as a standalone modular component, controller, or the like communicatively coupled to the system. An artificial intelligence program and/or machine learning program may generally be configured to perform methods and functions as described or implied herein, for example by one or more corresponding flow charts expressly provided or implied as would be understood by one of ordinary skill in the art to which the subjects matters of these descriptions pertain.

A machine learning program may be configured to implement stored processing, such as decision tree learning, association rule learning, artificial neural networks, recurrent artificial neural networks, long short term memory networks, inductive logic programming, support vector machines, clustering, Bayesian networks, reinforcement learning, representation learning, similarity and metric learning, sparse dictionary learning, genetic algorithms, k-nearest neighbor (KNN), and the like. In some embodiments, the machine learning algorithm may include one or more image recognition algorithms suitable to determine one or more categories to which an input, such as data communicated from a visual sensor or a file in JPEG, PNG or other format, representing an image or portion thereof, belongs. Additionally or alternatively, the machine learning algorithm may include one or more regression algorithms configured to output a numerical value given an input. Further, the machine learning may include one or more pattern recognition algorithms, e.g., a module, subroutine or the like capable of translating text or string characters and/or a speech recognition module or subroutine. In various embodiments, the machine learning module may include a machine learning acceleration logic, e.g., a fixed function matrix multiplication logic, in order to implement the stored processes and/or optimize the machine learning logic training and interface.

One type of algorithm suitable for use in machine learning modules as described herein is an artificial neural network or neural network, taking inspiration from biological neural networks. An artificial neural network can learn to perform tasks by processing examples, without being programmed with any task-specific rules. A neural network generally includes connected units, neurons, or nodes (e.g., connected by synapses) and may allow for the machine learning program to improve performance. A neural network may define a network of functions, which have a graphical relationship. As an example, a feedforward network may be utilized, e.g., an acyclic graph with nodes arranged in layers.

The artificial intelligence systems and structures discussed herein may employ deep learning. Deep learning typically employs a software structure comprising several layers of neural networks that perform nonlinear processing, where each successive layer receives an output from the previous layer. Generally, the layers include an input layer that receives raw data from a sensor, a number of hidden layers that extract abstract features from the data, and an output layer that identifies a certain thing based on the feature extraction from the hidden layers. The neural networks include neurons or nodes that each has a "weight" that is multiplied by the input to the node to obtain a probability of whether something is correct. More specifically, each of the nodes has a weight that is a floating point number that is multiplied with the input to the node to generate an output for that node that is some proportion of the input. The weights are initially "trained" or set by causing the neural networks to analyze a set of known data under supervised processing and through minimizing a cost function to allow the network to obtain the highest probability of a correct output.

Figures 2, 3, 4:
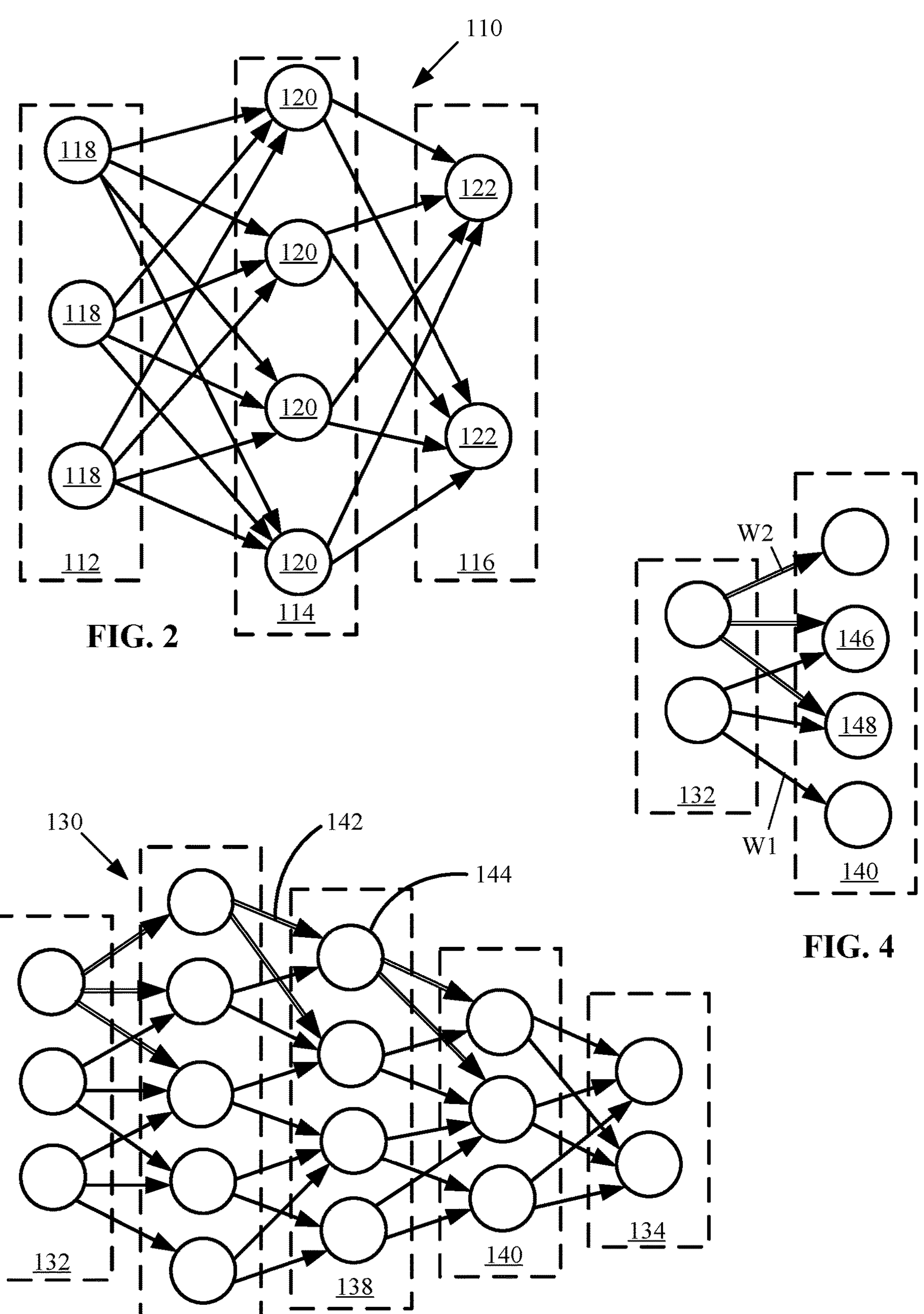
FIG. 2 is a diagram of a feedforward network.
FIG. 3 is a diagram of a convolutional neural network (CNN)
FIG. 4 is a diagram of a portion of the CNN shown in FIG. 3 illustrating assigned weights at connections or neurons.

FIG. 2 illustrates a feedforward neural network 110 that includes a hidden layer 114 between an input layer 112 and an output layer 116. The input layer 112, having nodes commonly referenced in FIG. 2 as input nodes 118 for convenience, communicates input data, variables, matrices, or the like to the hidden layer 114, having nodes 120. The hidden layer 114 generates a representation and/or transformation of the input data into a form that is suitable for generating output data. Adjacent layers of the neural network 110 are connected at the edges of the nodes of the respective layers, but nodes within a layer typically are not separated by an edge. In at least one embodiment of such a feedforward neural network, data is communicated to the nodes 118 of the input layer 112, which then communicates the data to the hidden layer 114. The hidden layer 114 may be configured to determine the state of the nodes in the respective layers and assign weight coefficients or parameters of the nodes based on the edges separating each of the layers, such as an activation function implemented between the input data communicated from the input layer 112 and the output data communicated to nodes 122 of the output layer 116. It should be appreciated that the form of the output from the neural network may generally depend on the type of model represented by the algorithm. Although the feedforward neural network 110 expressly includes a single hidden layer, other embodiments of feedforward networks within the scope of the descriptions can include any number of hidden layers. The hidden layers are intermediate the input and output layers and are generally where all or most of the computation is done.

Neural networks may perform a supervised learning process where known inputs and known outputs are utilized to categorize, classify, or predict a quality of a future input. However, additional or alternative embodiments of the machine learning program may be trained utilizing unsupervised or semi-supervised training, where none of the outputs or some of the outputs are unknown, respectively. Typically, a machine learning algorithm is trained, for example, utilizing a training data set, prior to modeling the problem with which the algorithm is associated. Supervised training of the neural network may include choosing a network topology suitable for the problem being modeled by the network and providing a set of training data representative of the problem. Generally, the machine learning algorithm may adjust the weight coefficients until any error in the output data generated by the algorithm is less than a predetermined, acceptable level. For instance, the training process may include comparing the generated output produced by the neural network in response to the training data with a desired or correct output. An associated error amount may then be determined for the generated output data, such as for each output data point generated in the output layer. The associated error amount may be communicated back through the system as an error signal, where the weight coefficients assigned in the hidden layer are adjusted based on the error signal. For instance, the associated error amount, such as a value between −1 and 1, may be used to modify the previous coefficient, e.g., a propagated value.

The machine learning algorithm may be considered sufficiently trained when the associated error amount for the output data is less than the predetermined, acceptable level, for example, each data point within the output layer includes an error amount less than the predetermined, acceptable level. Thus, the parameters determined from the training process can be utilized with new input data to categorize, classify, and/or predict other values based on the new input data.

An additional or alternative type of neural network suitable for use in a machine learning program and/or module is a convolutional neural network (CNN). A CNN is a type of feedforward neural network that may be utilized to model data associated with input data having a grid-like topology. In some embodiments, at least one layer of a CNN may include a sparsely connected layer, in which each output of a first hidden layer does not interact with each input of the next hidden layer. For example, the output of the convolution in the first hidden layer may be an input of the next hidden layer, rather than a respective state of each node of the first layer. CNNs are typically trained for pattern recognition, such as speech processing, language processing, and visual processing. As such, CNNs may be particularly useful for implementing optical and pattern recognition programs required from the machine learning model or program. A CNN includes an input layer, a hidden layer, and an output layer, typical of feedforward networks, but the nodes of a CNN input layer are generally organized into a set of categories via feature detectors and based on the receptive fields of the sensor, retina, input layer, etc. Each filter may then output data from its respective nodes to corresponding nodes of a subsequent layer of the network. A CNN may be configured to apply the convolution mathematical operation to the respective nodes of each filter and communicate the same to the corresponding node of the next subsequent layer. As an example, the input to the convolution layer may be a multidimensional array of data. The convolution layer, or hidden layer, may be a multidimensional array of parameters determined while training the model.

FIG. 3 is an illustration of an exemplary CNN 130 that includes an input layer 132 and an output layer 134. However, where the single hidden layer 114 is provided in the network 110, multiple consecutive hidden layers 136, 138 and 140 are provided in the CNN 130. Edge neurons 142 represented by white-filled arrows highlight that hidden layer nodes 144 can be connected locally, such that not all of the nodes of succeeding layers are connected by neurons.

FIG. 4 shows a portion of the CNN 130, specifically portions of the input layer 132 and the first hidden layer 136, and illustrates that connections can be weighted. In the illustrated example, labels W1 and W2 refer to respective assigned weights for the referenced connections. The two hidden nodes 146 and 148 share the same set of weights W1 and W2 when connecting to two local patches.

Figures 5, 6:
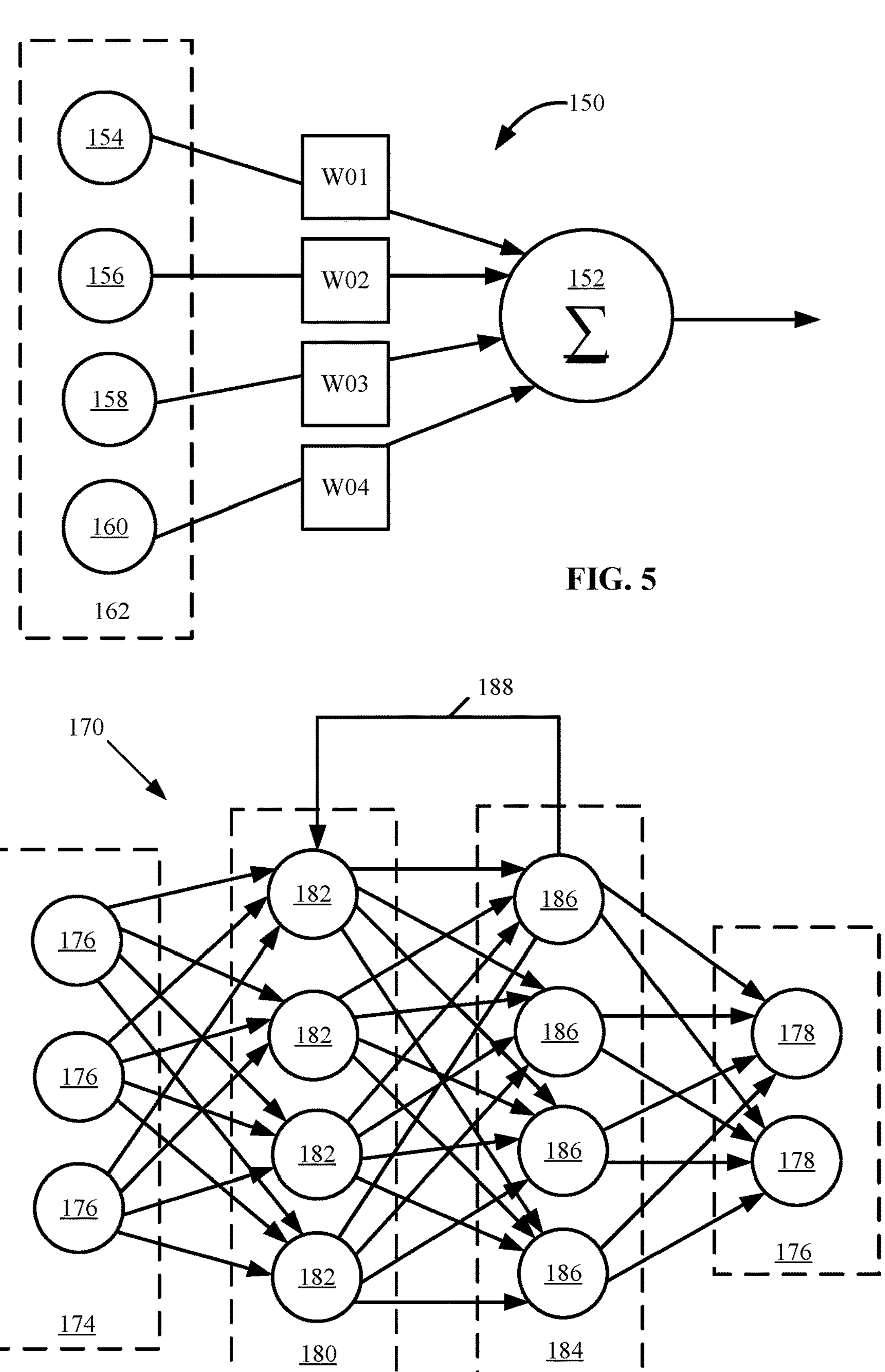
FIG. 5 is a diagram representing an exemplary weighted sum computation in a node in an artificial neural network.
FIG. 6 is a diagram of a recurrent neural network (RNN) utilized in machine learning.

A weight defines the impact a node in any given layer has on computations by a connected node in the next layer. FIG. 5 shows a network 150 including a node 152 in a hidden layer. The node 152 is connected to several nodes in the previous layer representing inputs to the node 152. Input nodes 154, 156, 158 and 160 in an input layer 162 are each assigned a respective weight W01, W02, W03, and W04 in the computation at the node 152, which in this example is a weighted sum.

An additional or alternative type of feedforward neural network suitable for use in the machine learning program and/or module is a recurrent neural network (RNN). An RNN may allow for analysis of sequences of inputs rather than only considering the current input data set. RNNs typically include feedback loops/connections between layers of the topography, thus allowing parameter data to be communicated between different parts of the neural network. RNNs typically have an architecture including cycles, where past values of a parameter influence the current calculation of the parameter, e.g., at least a portion of the output data from the RNN may be used as feedback/input in calculating subsequent output data. In some embodiments, the machine learning module may include an RNN configured for language processing, e.g., an RNN configured to perform statistical language modeling to predict the next word in a string based on the previous words. The RNN(s) of the machine learning model or program may include a feedback system suitable to provide the connection(s) between subsequent and previous layers of the network.

FIG. 6 illustrates an RNN 170 that includes an input layer 172 with nodes 174, an output layer 176 with nodes 178, and multiple consecutive hidden layers 180 and 182 with nodes 184 and nodes 186, respectively. The RNN 170 also includes a feedback connector 188 configured to communicate parameter data from at least one of the nodes 186 in the second hidden layer 184 to at least one of the nodes 182 in the first hidden layer 184. It should be appreciated that two or more and up to all of the nodes of a subsequent layer may provide or communicate a parameter or other data to a previous layer of the RNN 170. Moreover and in some embodiments, the RNN 170 may include multiple feedback connectors, such as connectors suitable to communicatively couple pairs of nodes and/or connector systems configured to provide communication between three or more nodes. Additionally or alternatively, the feedback connector 188 may communicatively couple two or more nodes having at least one hidden layer between them, i.e., nodes of non-sequential layers of the RNN 170.

In an additional or alternative embodiment, the machine learning program may include one or more support vector machines. A support vector machine may be configured to determine a category to which input data belongs. For example, the machine learning program may be configured to define a margin using a combination of two or more of the input variables and/or data points as support vectors to maximize the determined margin. Such a margin may generally correspond to a distance between the closest vectors that are classified differently. The machine learning program may be configured to utilize a plurality of support vector machines to perform a single classification. For example, the machine learning program may determine the category to which input data belongs using a first support vector determined from first and second data points/variables, and the machine learning program may independently categorize the input data using a second support vector determined from third and fourth data points/variables. The support vector machine(s) may be trained similarly to the training of neural networks, e.g., by providing a known input vector (including values for the input variables) and a known output classification. The support vector machine is trained by selecting the support vectors and/or a portion of the input vectors that maximize the determined margin.

As depicted, and in some embodiments, the machine learning program may include a neural network topography having more than one hidden layer. In such embodiments, one or more of the hidden layers may have a different number of nodes and/or the connections defined between layers. In some embodiments, each hidden layer may be configured to perform a different function. As an example, a first layer of the neural network may be configured to reduce a dimensionality of the input data, and a second layer of the neural network may be configured to perform statistical programs on the data communicated from the first layer. In various embodiments, each node of the previous layer of the network may be connected to an associated node of the subsequent layer (dense layers). Generally, the neural network(s) of the machine learning program may include a relatively large number of layers, e.g., three or more layers, and are referred to as deep neural networks. For example, the node of each hidden layer of a neural network may be associated with an activation function utilized by the machine learning program to generate an output received by a corresponding node in the subsequent layer. The last hidden layer of the neural network communicates a data set (e.g., the result of data processed within the respective layer) to the output layer. Deep learning neural networks may require more computational time and power to train, but the additional hidden layers provide multistep pattern recognition capability and/or reduced output error relative to simple or shallow machine learning architectures (e.g., including only one or two hidden layers).

Figure 7:
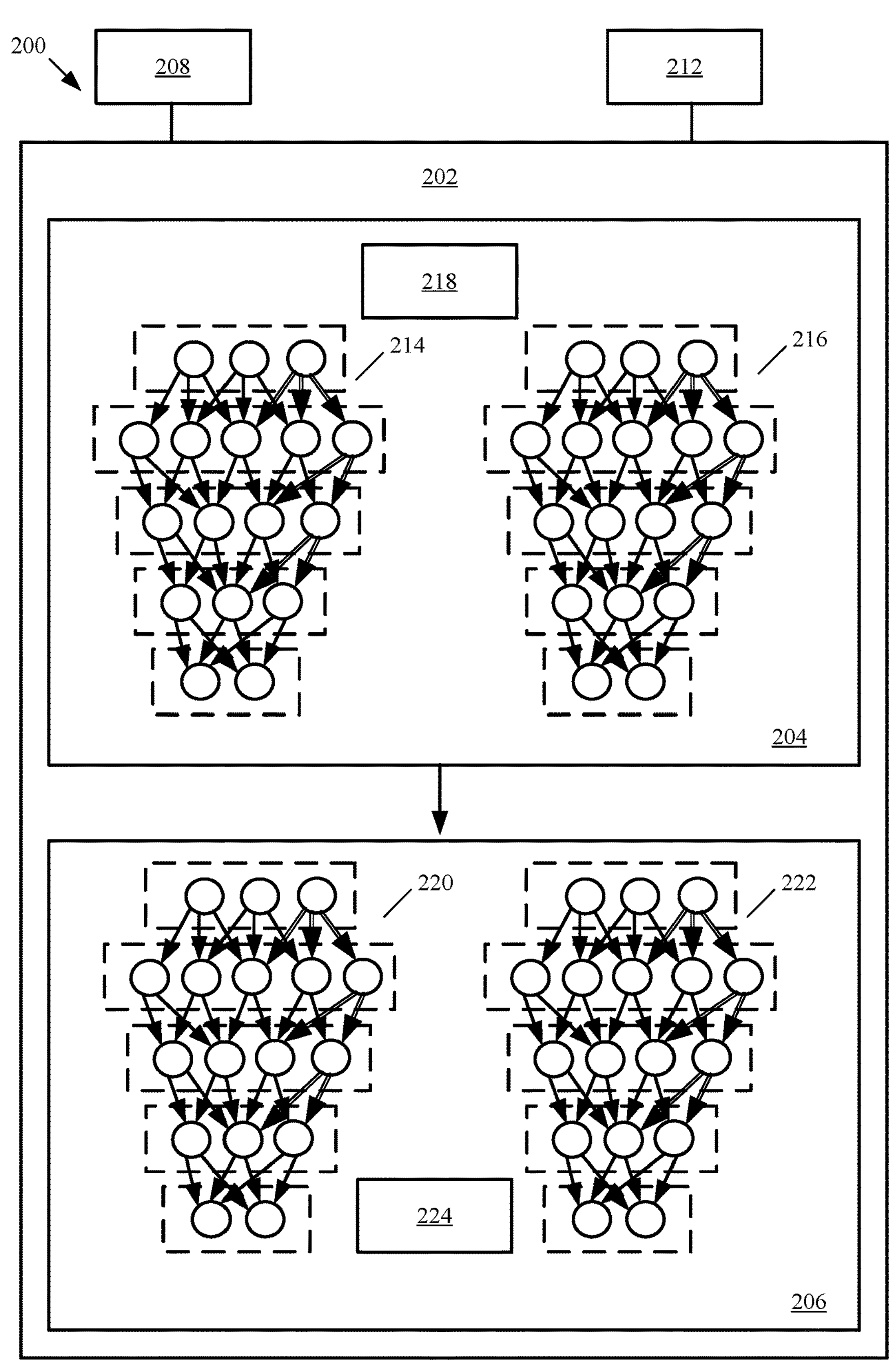
FIG. 7 is a schematic logic diagram of an artificial intelligence processor operating an artificial intelligence program.

FIG. 7 is a block diagram of an artificial intelligence programming system 200 including an AI processor 202, such as a dedicated processing device, that operates an artificial intelligence program, where the processor 202 includes a front-end sub-processor 204 and a back-end sub-processor 206. The algorithms associated with the front-end sub-processor 204 and the back-end sub-processor 206 may be stored in an associated memory device and/or storage device, such as memory device 208 communicatively coupled to the AI processor 202, as shown. Additionally, the system 200 may include a memory 212 storing one or more instructions necessary for operating the AI program. In this embodiment, the sub-processor 204 includes neural networks 214 and 216 operating an AI algorithm 218, such as feature recognition, and the sub-processor 206 includes neural networks 220 and 222 operating an AI algorithm 224 to perform an operation on the data set communicated directly or indirectly to the sub-processor 206.

The system 200 may provide statistical models or machine learning programs such as decision tree learning, associate rule learning, recurrent artificial neural networks, support vector machines, and the like. In various embodiments, the sub-processor 204 may be configured to include built in training and inference logic or suitable software to train the neural network prior to use, for example, machine learning logic including, but not limited to, image recognition, mapping and localization, autonomous navigation, speech synthesis, document imaging, or language translation. For example, the sub-processor 204 may be used for image recognition, input categorization, and/or support vector training. In various embodiments, the sub-processor 206 may be configured to implement input and/or model classification, speech recognition, translation, and the like.

For instance and in some embodiments, the system 200 may be configured to perform unsupervised learning, in which the machine learning model or program performs the training process using unlabeled data, e.g., without known output data with which to compare. During such unsupervised learning, the neural network may be configured to generate groupings of the input data and/or determine how individual input data points are related to the complete input data set. For example, unsupervised training may be used to configure a neural network to generate a self-organizing map, reduce the dimensionally of the input data set, and/or to perform outlier/anomaly determinations to identify data points in the data set that falls outside the normal pattern of the data. In some embodiments, the system 200 may be trained using a semi-supervised learning process in which some but not all of the output data is known, e.g., a mix of labeled and unlabeled data having the same distribution.

In some embodiments, the system 200 may include an index of basic operations, subroutines, and the like (primitives) typically implemented by AI and/or machine learning algorithms. Thus, the system 200 may be configured to utilize the primitives of the processor 202 to perform some or all of the calculations required by the system 200. Primitives suitable for inclusion in the processor 202 include operations associated with training a convolutional neural network (e.g., pools), tensor convolutions, activation functions, basic algebraic subroutines and programs (e.g., matrix operations, vector operations), numerical method subroutines and programs, and the like.

It should be appreciated that the machine learning model or program may include variations, adaptations, and alternatives suitable to perform the operations necessary for the system, and the present disclosure is equally applicable to such suitably configured machine learning and/or artificial intelligence programs, modules, etc. For instance, the machine learning program may include one or more long short-term memory (LSTM) RNNs, convolutional deep belief networks, deep belief networks DBNs, and the like. DBNs, for instance, may be utilized to pre-train the weighted characteristics and/or parameters using an unsupervised learning process. Further, the machine learning module may include one or more other machine learning tools (e.g., logistic regression (LR), Naive-Bayes, random forest (RF), matrix factorization, and support vector machines) in addition to, or as an alternative to, one or more neural networks, as described herein.

Figure 8:
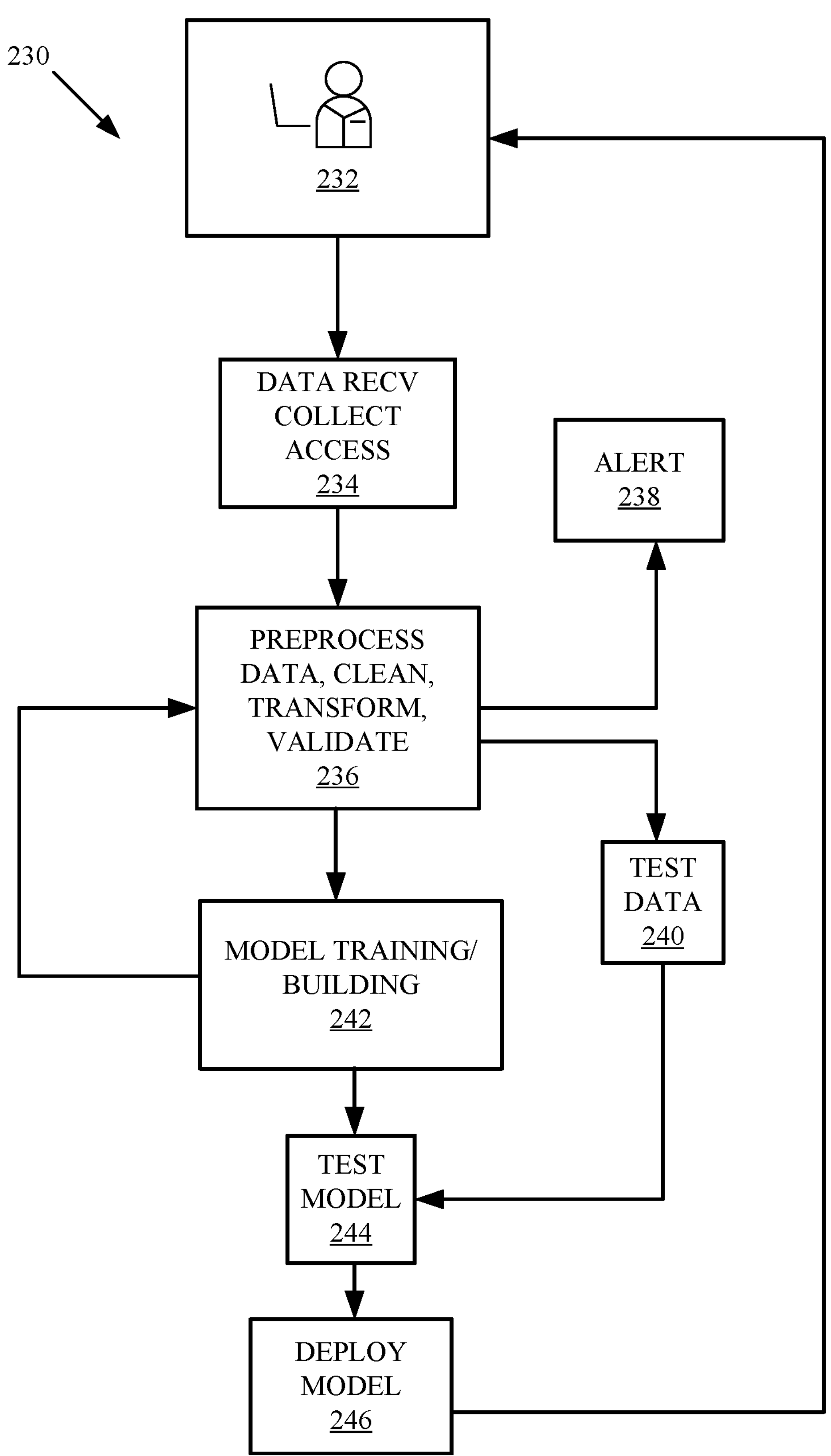
FIG. 8 is a flow chart showing a method for model development and deployment by machine learning.

FIG. 8 is a flow chart diagram 230 showing an exemplary method for model development and deployment by machine learning. The method represents at least one example of a machine learning workflow in which steps are implemented in a machine learning project. At box 232, a user authorizes, requests, manages, or initiates the machine-learning workflow. This may represent a user such as human agent, or customer, requesting machine-learning assistance or AI functionality to simulate intelligent behavior, such as a virtual agent, or other machine-assisted or computerized tasks that may, for example, entail visual perception, speech recognition, decision-making, translation, forecasting, predictive modelling, and/or suggestions as non-limiting examples. In a first iteration from the user perspective, the box 232 can represent a starting point. However, with regard to continuing or improving an ongoing machine learning workflow, the box 232 can represent an opportunity for further user input or oversight via a feedback loop.

At box 234, data is received, collected, accessed or otherwise acquired and entered as can be termed data ingestion. At box 236, data ingested from the box 234 is pre-processed, for example, by cleaning, and/or transformation such as into a format that the following components can digest. The incoming data may be versioned to connect a data snapshot with the particularly resulting trained model. As newly trained models are tied to a set of versioned data, preprocessing steps are tied to the developed model. If new data is subsequently collected and entered, a new model will be generated. If the preprocessing is updated with newly ingested data, an updated model will be generated. The process at the box 236 can include data validation, which focuses on confirming that the statistics of the ingested data are as expected, such as that data values are within expected numerical ranges, that data sets are within any expected or required categories, and that data comply with any needed distributions such as within those categories. The process can proceed to box 238 to automatically alert the initiating user, other human or virtual agents, and/or other systems, if any anomalies are detected in the data, thereby pausing or terminating the process flow until corrective action is taken.

At box 240, training test data, such as a target variable value, is inserted into an iterative training and testing loop. At box 242, model training, a core step of the machine learning work flow, is implemented. A model architecture or neural network simulation model is trained in the iterative training and testing loop. For example, features in the training test data are used to train the model based on weights and iterative calculations in which the target variable may be incorrectly predicted in an early iteration as determined by comparison at box 244, where the model is tested. Subsequent iterations of the model training at the box 242 may be conducted with updated weights in the calculations.

When compliance and/or success in the model testing at the box 244 is achieved, the process proceeds to box 246, where model deployment is triggered. The model may be utilized in AI functions and programming, for example, to simulate intelligent behavior, to perform machine-assisted or computerized tasks, of which visual perception, speech recognition, decision-making, translation, forecasting, predictive modelling, and/or automated suggestion generation serve as non-limiting examples.

Figure 9:
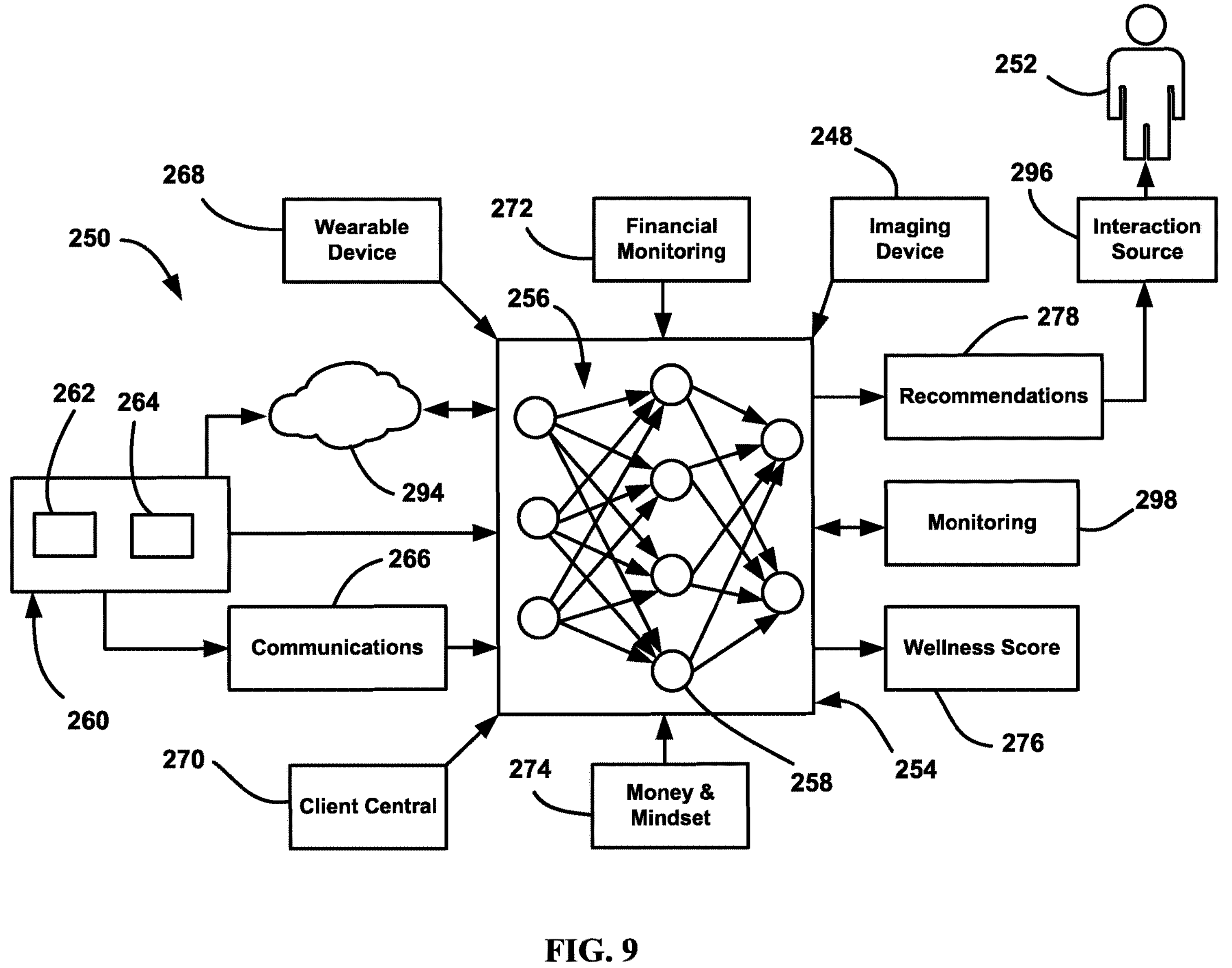
FIG. 9 an illustration of an architecture for a combined financial and wellness scoring system that evaluates and monitors the financial and physical wellbeing of a person.

FIG. 9 is an illustration of an architecture of a combined financial and wellness scoring system 250 that evaluates and monitors the financial and physical wellbeing of a person 252, such as a client of a bank, and provides recommendations to the person 252 for banking products and services that may improve the health and wellbeing of the person 252. The system 250 may be part of the enterprise system 12 and may employ some or any of the devices and processes discussed above. The combined financial and physical wellbeing of the person 252 is determined by an AI processor 254 that employs machine learning and receives data and information from various sources, as will be discussed in detail below. Thus, the processor 254 may include, among other devices and components, one or more neural networks 256 having trained and weighted nodes 258. The nodes 258 in the neural network 256 would be weighted and trained for determining and monitoring the financial and physical wellbeing of the person 252 as discussed herein. As more information is learned about the person 252, the weights of the nodes 258 are tuned so that the processor 254 is better and more accurately able to determine the wellbeing of the person 252. Further, the processor 254 may also receive data and information about other bank client's that also may help teach and tune the processor 254 to identify the financial and physical wellbeing of the person 252.

As discussed above, machine learning is a type of artificial intelligence that allows various software applications to become more accurate at predicting outcomes without being explicitly programmed to do so, where the machine learning algorithms use historical data as an input to predict new output values. The machine learning processors, models, programs and algorithms used by the processor 254 for the purposes discussed herein can employ some, any or all of the various machine learning processing discussed above. For example, the processor 254 may include and/or employ deep learning, CNNs, RNNs, KNN, long short-term memory (LSTM) RNNs, decision tree learning, association rule learning, artificial neural networks, recurrent artificial neural networks, long short term memory networks, inductive logic programming, support vector learning and machines, clustering, Bayesian networks, reinforcement learning, representation learning, similarity and metric learning, sparse dictionary learning, genetic algorithms, machine learning acceleration logic, supervised neural network node training and learning, un-supervised neural network node training and learning, semi-supervised neural network node training and learning, shallow machine learning architectures, feature and image recognition, interference logic, logistic regression (LR), Naive-Bayes, random forest (RF), matrix factorization, etc.

The system 250 includes a wearable device 260, for example, fitness trackers, smart watches, connected headsets, smart glasses, wrist bands, etc. that the person 252 wears and that monitors various and several physiological stress or other factors of the person 252, such as heart rate, respiration rate, changes in skin condition, such as from sweating and temperature changes, alterations in sleep patterns, such as difficulty in sleeping and restlessness, blood pressure, diet-related factors, muscle tension and pain, body temperature, oxygen saturation, etc., sometimes referred generally herein as vital signs, through suitable sensors and detectors 262 on the device 260. The data and information obtained by the sensors and detectors 262 can be stored in a database or memory 264 in the device 260 and be periodically uploaded to a communications device 266 through, for example, Bluetooth or WiFi that subsequently sends the data and information to the processor 254 directly or through, for example, the Cloud 294. Alternately, the data and information stored in the memory 264 can be directly sent to the processor 254 through the Cloud 294 using, for example, cellular signal processing. This data and information is processed by the processor 254 as it is being received over time using machine learning for training and revising the weights of the nodes 258 in the neural network 256 consistent with the discussion herein to ascertain and monitor the physical and mental wellbeing of the person 252 and identify financial stress factors. Further, the AI processor 254 may be receiving data and information from wearable devices worn by other people, which is also used to tune the nodes 258 so that much more data can be used to identify the financial and physical health of the person 252.

In one embodiment, the wearable device 260 is provided by the bank when the person 252 enrolls in a certain program that the bank may offer for the sole purpose of monitoring physical and financial stress factors of the person so as to identify a financial wellness of the person 252 in the manner described herein.

In addition to or instead of the wearable device 260, the person 252 may be wearing a third-party wearable device 268 of the same or similar type as the device 260 that provides data about the person 252 to the processor 254 in the same or a similar manner as the device 260. The device 260 may be more specific to monitoring things that are more affected by financial issues and the third-party device 268 may be for another specific purpose such as monitoring blood sugar.

The system 250 also includes an imaging device 248, such as a 2D or 3D camera, that can be used to provide images of the person 252 to the processor 254 for image and feature recognition purposes. The feature recognition of the images can identify, for example, features of the face of the person 252 that may indicate stress or other health factors. The processor 254 may employ learned-based neural networks that extract gradients, edges, contours, elementary shapes, etc. from the images and provide image segmentation to identify the features. The images from the device 248 can be provided to the processor 254 in any suitable manner, such as those described above in connection with the wearable device 260. The device 248 can be provided by the bank as a package with the device 260 for monitoring the physical and financial wellbeing of the person 252.

The system 250 also includes a client central database 270, for example, an enterprise data lake (EDS), representing one or more sources of client data and information that is provided to the processor 254 possibly through the Cloud 294 that then uses this information to help determine the financial wellbeing or financial stress or anxiety of the person 252. One of those sources could be a customer information file (CIF) database, which is a client master database that stores identifying data and information, such as name, address, birth date, account types, account balances, social security number, credit score, etc., for all of the clients of the bank.

The system 250 also includes a financial monitoring source 272 that monitors various financial factors and positions of the person 252 and sends that information to the processor 254 possibly through the Cloud 294 to help determine the financial wellbeing or financial stress or anxiety of the person 252. These financial factors are obtained by any interaction that occurs between the person 252 and the banks representatives through any system or device, such as a client interaction and transaction source that stores information and data in a useable format obtained for each of the interactions and transactions between all of the banks clients and the bank over all of the banking channels. As used herein, an interaction or transaction is any event or action that occurs between a client of the bank and the bank or its representatives through any system or device, and a banking channel is a specific connection point for that interaction or transaction, such as a website, mobile applications, branch banking, online banking, customer service center calls, etc. These financial factors may include, but are not limited to, significant credit score changes, changes in direct deposit patterns or income changes from, for example, loss of employment, reduction in work hours, etc., changes in transaction and account patterns from, for example, account closure, frequent overdrafts, late payments, sudden increase in debt-related transactions, etc., changes in credit card patterns from, for example, increased transaction frequency for basic needs with decreased spending in dining out and entertainment, sale of investments or assets, requests for payment extensions or loan modifications, payday loans or cash advances, the number of credit cards that the person 252 has, etc.

The system 250 further includes a money and mindset source 274, such as a podcast or website, that identifies the financial literacy of the person 252 and sends data and information to the processor 254 possibly through the Cloud 294. Money and mindset refers to the beliefs, attitudes and thoughts a person has about money and wealth, and encompasses thoughts about a person's ability to earn, save, invest and manage money effectively.

The processor 254 receives and processes the data and information as it is being received over time from the various financial sources as described above and generates a financial wellbeing score for the person 252. The financial wellbeing score may be used to determine whether the bank can or cannot provide certain bank products and/or services to the person 252, such as providing a loan. The processor 254 also receives and processes the data and information from the devices 248, 260 and/or 268 as the data is being received over time and generates a physical or health wellbeing score. The financial wellbeing score and the health wellbeing score are then combined to obtain a care score or financial wellness score provided at box 276, which offers a comprehensive view of the person's financial wellbeing and provides a holistic measure of both economic health and physical, mental and emotional wellness. For example, the processor 254 may provide a score scale of 1-1000. Based on the data and information provided, the processor 254 may determine that the person's financial wellbeing score is 450 and the person's health wellbeing score is 730 on that scale. The financial wellness score is then (450+730)/2=590.

Once the financial wellness score is obtained, a bank representative, or some other bank resource, can then contact the person 252 to recommend personalized banking products and services at box 278 to the person 252 based on that score, thus possibly providing a targeted and effective enhancement of the person's quality of life. For example, if the financial wellness score is low, then one class of banking products and services may be recommended, which may require more urgent action by the person 252, and if the financial wellness score is high, then another class of banking products and services may be recommended. Those recommendations may include one or more of AI financial planning and advisory services, AI health and wellness advisor, dedicated financial advisors, flexible loan options, high-yield savings accounts, low interest credit cards, etc. The recommendations can be provided to the person 252 in any suitable manner, such as through personal client interaction by a representative of the bank, for example, a personal banker or a relationship banker, a banking website, mobile phone, ChatGPT, which is a language model that steers conversations to a desired goal, etc., generally represented by box 296.

The person 252 will be continuously monitored by the processor 254 at box 298 in the manner discussed above over time to observe changes of the financial wellness score of the person 252 including the impact that the recommended banking products and services have on the person 252. As the data and information is provided to the processor 254, the machine learning processes learn more about the person 252 so that the processor 254 is tuned to more accurately determine the financial wellbeing of the person 252. The recommendations of banking products and services can be updated as necessary as the various financial positions, stress factors and attributes of the person 252 are further monitored and identified for financial and health wellbeing. Thus, as the person 252 may use the recommended products and/or services, the wellness score can be observed and monitored to see how the products and/or services impact the person's wellness and can be updated accordingly. Further, as the person 252 moves through time and his/her financial wellbeing changes based on whatever factors affect the person 252, such as a new hardship, the data and information that is received by the processor 254 will track these factors accordingly and the machine learning model and algorithms employed in the processor 254 will be updated and tuned accordingly to more accurately identify what new and different products and services may benefit the person 252.

Figure 10:
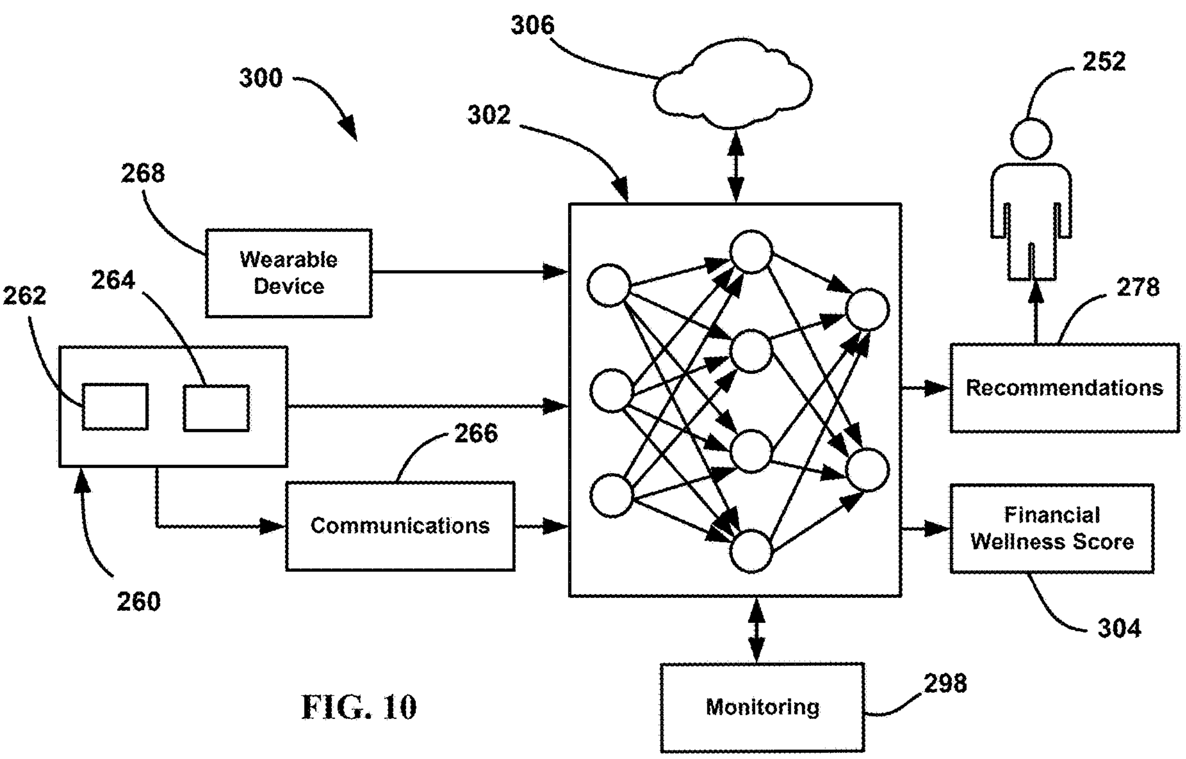
FIG. 10 is an illustration of an architecture of a financial wellness scoring system that monitors the financial wellness of a person wearing a device that monitors the person's vital signs and other physical attributes.

In an alternate embodiment, the wearable device 260 and/or the third party device 268 can be used alone to identify the financial wellness of the person 252. In this embodiment, the devices 260 and 268 may be more specific to monitoring things that are more affected by financial stress on the person 252. FIG. 10 is an illustration of an architecture of a financial wellness scoring system 300 that evaluates and monitors the financial wellness of the person 252 showing this embodiment, where like elements to the system 250 are identified by the same reference number. The system 300 may be part of the enterprise system 12 and may employ some or any of the devices and processes discussed above. The data and information provided by the device 260 and/or the device 268 is processed by an AI processor 302 in the same or similar manner as the processor 254, and that provides a financial wellness score of the person 252 at box 304. The processor 302 may receive data and information from various sources 306, such as those discussed above, and may include calculations of the financial wellness score of other people.

Figure 11:
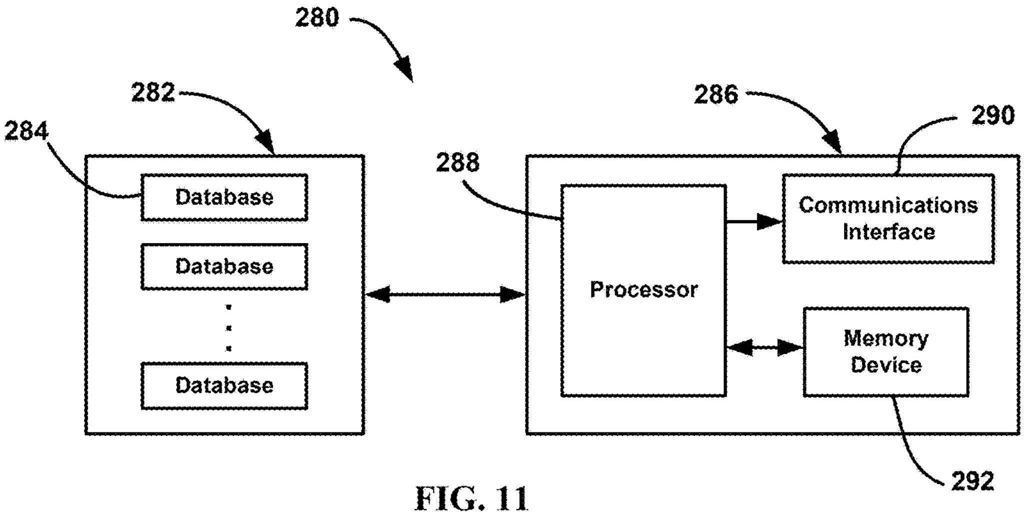
FIG. 11 is a block diagram of an architecture that could be part of a combined financial and wellness scoring system or financial wellness scoring system that evaluates and monitors the financial wellness of a person.

FIG. 11 is a block diagram of an architecture 280 that could be part of the enterprise system 12 and could be part of the financial and wellness scoring system 250 that evaluates and monitors the financial and physical wellness of the person 252, as discussed above. The architecture 280 includes a repository 282 having a plurality of databases 284 that store data and information in a format accessible to users, and a back-end server 286 operatively coupled to the repository 282 and being responsive to the data and information from all of the databases 284. The back-end server 286 includes a processor 288 for processing the data and information, a communications interface 290 communicatively coupled to the processor 288 and a memory device 292 for storing data and executable code. The executable code causes the processor 288 to collect data and information from the databases 284, store the collected data and information in the memory device 292, process the stored data and information through a machine learning model, receive a result from the machine learning model, and transmit a communication identifying the result on the interface 290.

Particular embodiments and features have been described with reference to the drawings. It is to be understood that these descriptions are not limited to any single embodiment or any particular set of features. Similar embodiments and features may arise or modifications and additions may be made without departing from the scope of these descriptions and the spirit of the appended claims.

What is claimed is:

1. A computer system, comprising:
- at least one processor;
- a communications interface communicatively coupled to the at least one processor; and
- a memory device storing executable code that, when executed, causes the at least one processor to:
  - train, using training test data, a first neural network to predict factors indicative of a financial stress level, the training including:
    - iteratively predicting the factors from the training test data that correlate to the financial stress, the predicting generating a prediction;
    - testing and comparing, during each iteration, the prediction to a target variable; and
    - indicating, for each iteration and via a feedback loop, modifications to weights assigned to nodes of the first neural network to improve the first neural network's ability to predict the target variable and reduce error of the prediction;
  - deploy the trained first neural network;
  - collect financial data about a first factor of a person, the first factor being indicative of the person's financial wellbeing;
  - generate, from the financial data, a first score associated with the first factor, the first score being correlated to a user profile of the person;
  - train a second neural network to extract gradients, edges, and contours from images and to perform image segmentation to identify features of a face that indicate stress;
  - collect, from one or more devices, data indicative of a second factor of the person, the second factor being indicative of the person's physical wellbeing, the one or more devices including (a) a wearable device worn by the person that detects physiological stress indicators including one or more of (i) heart rate variability, (ii) changes in skin condition from sweating or temperature changes, and (iii) alterations in sleep patterns, and (b) an imaging device that captures one or more images of the person;
  - process, via the second neural network, the one or more images to implement the image segmentation to identify facial features of the face of the person indicative of the person's stress from the one or more images;
  - process the physiological stress indicators indicative of financial stress;
  - generate, from the identified facial features and the processed physiological stress indicators, a second score associated with the second factor, the second score being correlated to the user profile of the person;
  - predict, via the deployed first neural network and based on the first score and the second score, the person's financial stress level, the predicted financial stress level being a financial wellness score;
  - assign the financial wellness score to the user profile;
  - identify, based on the assigned financial wellness score, and transmit, via the communications interface, one or more recommendations to a device associated with the person; and
  - track an impact of the one or more recommendations on the person's financial wellness score, and based thereon continuously update the weights of the nodes of the first neural network based on the assigned financial wellness score to improve subsequent predictions for the person;
  - wherein the user profile is associated with a banking system of a bank based on the person being a client of the bank; and
  - wherein at least some of the financial data is obtained from a financial monitoring source that provides information associated with one or more of (i) credit score changes, (ii) changes in direct deposit patterns or income changes including loss of employment and reduction in work hours, (iii) changes in transaction and account patterns including account closures, (iv) overdrafts, late payments and an increase in debt-related transactions, (v) changes in credit card patterns including increased transaction frequency for basic needs with decreased spending in dining out and entertainment, (vi) sale of investments or assets, (vii) requests for payment extensions or loan modifications, and (viii) payday loans or cash advances.

2. The system according to claim 1 wherein the at least one processor collects additional financial information of the person from a client central database that stores name, address, birthdate, account types, account balances, social security number and credit scores for clients of the bank and incorporates the additional financial information as part of the financial data.

3. The system according to claim 1 wherein the at least one processor collects additional financial information of the person from a client interaction and transaction source that stores information and data obtained for interactions and transactions between the bank's clients and the banking system over banking channels.

4. The system according to claim 1 wherein the at least one processor collects additional financial information of the person from a money and mindset source that provides a determination of the financial literacy of the person.

5. The system according to claim 1 wherein the wearable device detects one or more of heart rate, respiration rate, changes in skin condition including from sweating and temperature changes, alterations in sleep patterns including difficulty in sleeping and restlessness, blood pressure, diet-related factors, muscle tension and pain, body temperature, oxygen saturation and blood sugar.

6. The system according to claim 1 wherein the wearable device is one of a fitness tracker, a smart watch, a connected headset, smart glasses or a wrist band.

7. The system according to claim 1 wherein the wearable device is provided by the bank or provided by a third-party or both.

8. The system according to claim 1 wherein the banking system provides recommendations for bank products and/or services based on the financial wellness score.

9. The system according to claim 8 wherein the at least one processor continuously determines and updates the financial wellness score including after the person has implemented one or more of the recommendations for the bank products and/or services.

10. The system according to claim 1 wherein the first and/or second neural networks are a convolutional neural network (CNN) or a recurrent neural network (RNN).

11. A computer-implemented method, said method comprising:

training, using training test data, a first neural network to predict factors indicative of a financial stress level, the training including:

iteratively predicting the factors from the training test data that correlate to the financial stress, the predicting generating a prediction;

testing and comparing, during each iteration, the prediction to a target variable; and indicating, for each iteration and via a feedback loop, modifications to weights assigned to nodes of the first neural network to improve the first neural network's ability to predict the target variable and reduce error of the prediction;

deploying the trained first neural network;

collecting financial data about a first factor of a person, the first factor being indicative of the person's financial wellbeing;

generating, from the financial data, a first score associated with the first factor, the first score being correlated to a user profile of the person;

training a second neural network to extract gradients, edges, and contours from images and to perform image segmentation to identify features of a face that indicate stress;

collecting, from one or more devices, data indicative of a second factor of the person, the second factor being indicative of the person's physical wellbeing, the one or more devices including (a) a wearable device worn by the person that detects physiological stress indicators including one or more of (i) heart rate variability, (ii) changes in skin condition from sweating or temperature changes, and (iii) alterations in sleep patterns, and (b) an imaging device that captures one or more images of the person;

processing, via the second neural network, the one or more images to implement the image segmentation to identify facial features of the face of the person indicative of the person's stress from the one or more images;

processing the physiological stress indicators indicative of financial stress;

generating, from the identified facial features and the processed physiological stress indicators, a second score associated with the second factor, the second score being correlated to the user profile of the person;

predicting, via the deployed first neural network and based on the first score and the second score, the person's financial stress level, the predicted financial stress level being a financial wellness score;

assigning the financial wellness score to the user profile;

identifying, based on the assigned financial wellness score, and transmitting, via the communications interface, one or more recommendations to a device associated with the person; and tracking an impact of the one or more recommendations on the person's financial wellness score, and based thereon continuously updating the weights of the nodes of the first neural network based on the assigned financial wellness score to improve subsequent predictions for the person;

wherein the user profile is associated with a banking system of a bank based on the person being a client of the bank; and wherein at least some of the financial data is obtained from a financial monitoring source that provides information associated with one or more of (i) credit score changes, (ii) changes in direct deposit patterns or income changes including loss of employment and reduction in work hours, (iii) changes in transaction and account patterns including account closures, (iv) overdrafts, late payments and an increase in debt-related transactions, (v) changes in credit card patterns including increased transaction frequency for basic needs with decreased spending in dining out and entertainment, (vi) sale of investments or assets, (vii) requests for payment extensions or loan modifications, and (viii) payday loans or cash advances.

12. The method according to claim 11 wherein the method continuously determines and updates the financial wellness score including after the person has implemented one or more recommendations for bank products and/or services.

13. The method according to claim 11, further including collecting additional financial information of the person from a client central database that stores name, address, birthdate, account types, account balances, social security number and credit scores for clients of the bank and incorporates the additional financial information as part of the financial data.

14. The method according to claim 11, further including collecting additional financial information of the person from a client interaction and transaction source that stores information and data obtained for interactions and transactions between the bank's clients and the banking system over banking channels.

15. A non-transitory computer-readable storage medium, the computer-readable storage medium including instructions that, when executed by a processor, cause the processor to:

train, using training test data, a first neural network to predict factors indicative of a financial stress level, the training including:

iteratively predicting the factors from the training test data that correlate to the financial stress, the predicting generating a prediction;

testing and comparing, during each iteration, the prediction to a target variable; and indicating, for each iteration and via a feedback loop, modifications to weights assigned to nodes of the first neural network to improve the first neural network's ability to predict the target variable and reduce error of the prediction;

deploy the trained first neural network;

collect financial data about a first factor of a person, the first factor being indicative of the person's financial wellbeing;

generate, from the financial data, a first score associated with the first factor, the first score being correlated to a user profile of the person;

train a second neural network to extract gradients, edges, and contours from images and to perform image segmentation to identify features of a face that indicate stress;

collect, from one or more devices, data indicative of a second factor of the person, the second factor being indicative of the person's physical wellbeing, the one or more devices including (a) a wearable device worn by the person that detects physiological stress indicators including one or more of (i) heart rate variability, (ii) changes in skin condition from sweating or temperature changes, and (iii) alterations in sleep patterns, and (b) an imaging device that captures one or more images of the person;

process, via the second neural network, the one or more images to implement the image segmentation to identify facial features of the face of the person indicative of the person's stress from the one or more images;

process the physiological stress indicators indicative of financial stress;

generate, from the identified facial features and the processed physiological stress indicators, a second score associated with the second factor, the second score being correlated to the user profile of the person;

predict, via the deployed first neural network and based on the first score and the second score, the person's financial stress level, the predicted financial stress level being a financial wellness score;

assign the financial wellness score to the user profile;

identify, based on the assigned financial wellness score, and transmit, via the communications interface, one or more recommendations to a device associated with the person; and track an impact of the one or more recommendations on the person's financial wellness score, and based thereon continuously update the weights of the nodes of the first neural network based on the assigned financial wellness score to improve subsequent predictions for the person;

wherein the user profile is associated with a banking system of a bank based on the person being a client of the bank, and wherein at least some of the financial data is obtained from a financial monitoring source that provides information associated with one or more of (i) credit score changes, (ii) changes in direct deposit patterns or income changes including loss of employment and reduction in work hours, (iii) changes in transaction and account patterns including account closures, (iv) overdrafts, late payments and an increase in debt-related transactions, (v) changes in credit card patterns including increased transaction frequency for basic needs with decreased spending in dining out and entertainment, (vi) sale of investments or assets, (vii) requests for payment extensions or loan modifications, and (viii) payday loans or cash advances.

16. The computer-readable storage medium of claim 15, wherein the processor is further caused to collect additional financial information of the person from a client central database that stores name, address, birthdate, account types, account balances, social security number and credit scores for clients of the bank and incorporates the additional financial information as part of the financial data.

17. The computer-readable storage medium of claim 15, wherein the processor is further caused to collect additional financial information of the person from a client interaction and transaction source that stores information and data obtained for interactions and transactions between the bank's clients and the banking system over banking channels.

18. The computer-readable storage medium of claim 15, wherein the processor is further caused to collect additional financial information of the person from a money and mindset source that provides a determination of the financial literacy of the person.

19. The computer-readable storage medium of claim 15, wherein the wearable device detects one or more of heart rate, respiration rate, changes in skin condition including from sweating and temperature changes, alterations in sleep patterns including difficulty in sleeping and restlessness, blood pressure, diet-related factors, muscle tension and pain, body temperature, oxygen saturation and blood sugar.

20. The computer-readable storage medium of claim 15, wherein the wearable device is one of a fitness tracker, a smart watch, a connected headset, smart glasses or a wrist band.

* * * * *